United States Patent
Rogers et al.

(10) Patent No.: US 6,958,073 B2
(45) Date of Patent: Oct. 25, 2005

(54) METHOD AND SYSTEM FOR STENT RETENTION USING AN ADHESIVE

(75) Inventors: Ronan Rogers, Galway (IE); Susheel R. Deshmukh, Santa Rosa, CA (US); Kaushik A. Patel, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/823,216

(22) Filed: Apr. 13, 2004

(65) Prior Publication Data

US 2004/0210299 A1    Oct. 21, 2004

Related U.S. Application Data

(63) Continuation-in-part of application No. 10/419,457, filed on Apr. 21, 2003.

(51) Int. Cl.$^7$ ............................................. A61M 29/00
(52) U.S. Cl. ..................... 606/194; 606/191; 606/192; 606/198; 606/108; 623/1.11; 623/1.12; 623/1.19; 623/1.21
(58) Field of Search .............................. 623/1.11, 1.12, 623/1.19, 1.21; 606/108, 191–198

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,674,242 A * | 10/1997 | Phan et al. | 606/198 |
| 6,066,156 A * | 5/2000 | Yan | 606/192 |
| 6,090,127 A | 7/2000 | Globerman | |
| 6,159,229 A * | 12/2000 | Jendersee et al. | 606/198 |
| 6,666,880 B1 * | 12/2003 | Chiu et al. | 623/1.11 |
| 6,682,553 B1 * | 1/2004 | Webler, Jr. | 623/1.11 |

* cited by examiner

*Primary Examiner*—Glenn K. Dawson
*Assistant Examiner*—Michael G. Mendoza

(57) ABSTRACT

The invention provides a method of manufacturing a system for treating a vascular condition. A catheter including an inflatable balloon is provided. A stent is positioned over the balloon. An adhesive material is applied between an inner surface of the stent and an outer surface of the balloon. The adhesive material is heated to above a melting point of the adhesive material. The adhesive material is cooled to below a melting point of the adhesive material to provide an adhesive bond that retains the stent to the catheter during vascular delivery, wherein the stent is released from the balloon following inflation and deflation of the balloon at a treatment site.

4 Claims, 4 Drawing Sheets

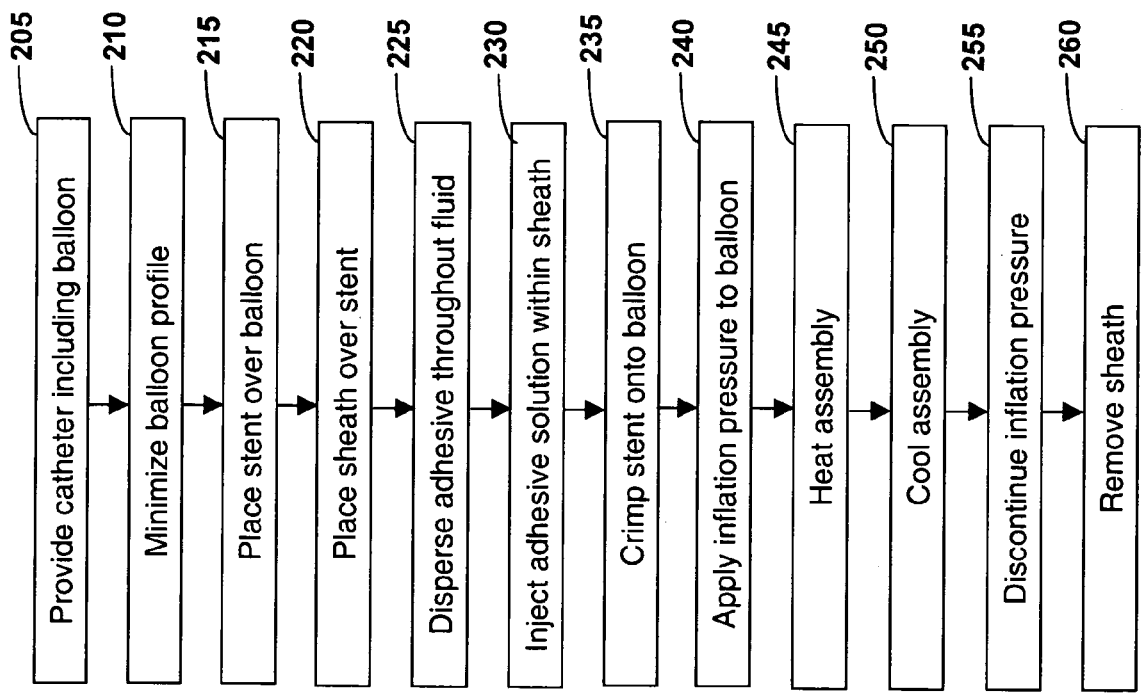

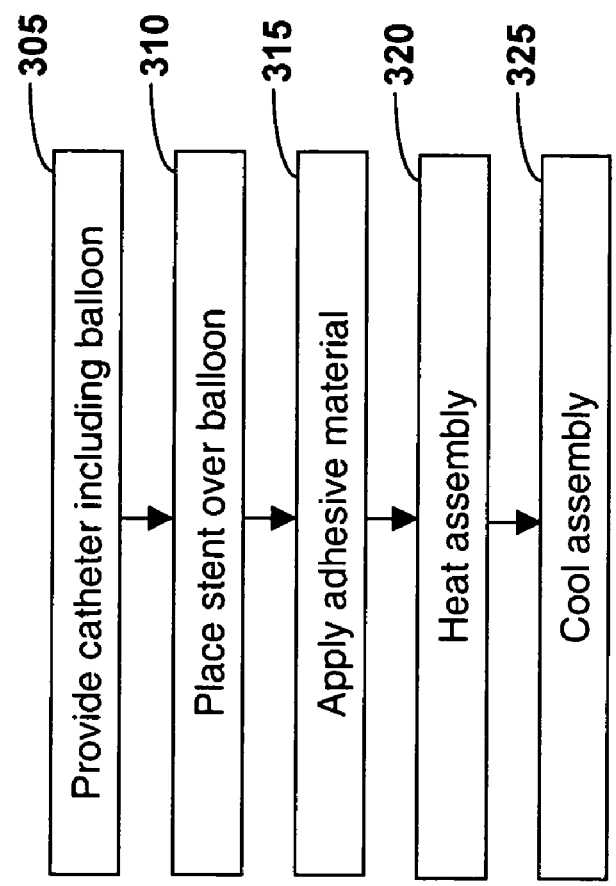

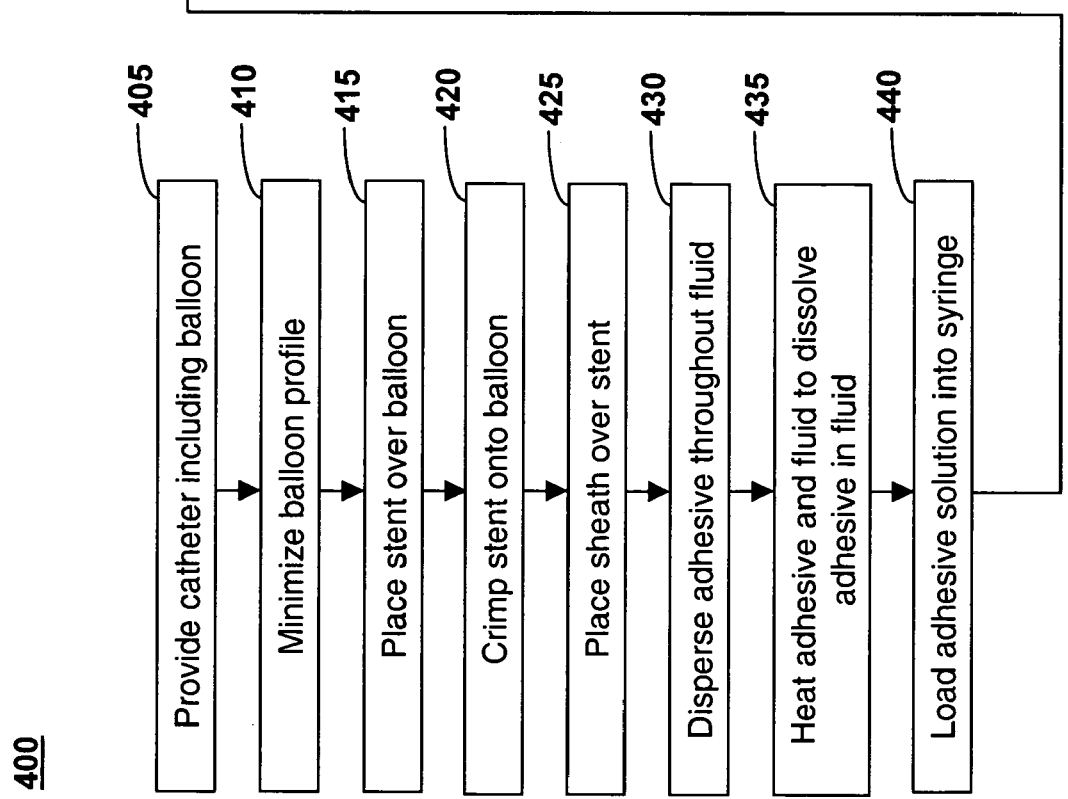

METHOD AND SYSTEM FOR STENT RETENTION USING AN ADHESIVE

PRIORITY CLAIM

This application is a continuation-in-part of U.S. application Ser. No. 10/419,457 filed Apr. 21, 2003, the entirety of which is hereby incorporated by reference.

TECHNICAL FIELD

This invention relates generally to biomedical devices that are used for treating vascular conditions. More specifically, the invention relates to using an adhesive to improve retention of a stent to a balloon catheter.

BACKGROUND OF THE INVENTION

Stents are generally cylindrical-shaped devices that are radially expandable to hold open a segment of a vessel or other anatomical lumen after implantation into the body lumen.

Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guide wire that is part of the delivery device. After the stent is positioned across the lesion, it is expanded by the delivery device, causing the length of the stent to contract and the diameter to expand. For a self-expanding stent, commonly a sheath is retracted, allowing expansion of the stent.

Stents are used in conjunction with balloon catheters in a variety of medical therapeutic applications, including intravascular angioplasty. For example, a balloon catheter device is inflated during percutaneous transluminal coronary angioplasty (PTCA) to dilate a stenotic blood vessel. The stenosis may be the result of a lesion such as a plaque or thrombus. When inflated, the pressurized balloon exerts a compressive force on the lesion, thereby increasing the inner diameter of the affected vessel. The increased interior vessel diameter facilitates improved blood flow. Soon after the procedure, however, a significant proportion of treated vessels restenose.

To prevent restenosis, a stent, constructed of a metal or polymer, is implanted within the vessel to maintain lumen size. The stent acts as a scaffold to support the lumen in an open position. Configurations of stents include a cylindrical tube defined by a mesh, interconnected stents, or like segments. Exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau.

For a stent to provide the desired beneficial effect, it must be delivered to precisely the correct position within a vessel. Disadvantages of some prior art stent delivery systems include difficulty maintaining the stent on the delivery catheter while advancing the stent to and through the target treatment site and difficulty releasing the stent once it is in place within the vessel.

Therefore, it would be desirable to provide a method and system for retaining a stent to a catheter for delivery and deployment of the stent in a vessel that overcomes the aforementioned and other disadvantages.

SUMMARY OF THE INVENTION

One aspect of the present invention is a method of manufacturing a system for treating a vascular condition. A catheter including an inflatable balloon is provided. A stent is positioned over the balloon. An adhesive material is applied between an inner surface of the stent and an outer surface of the balloon. The adhesive material is heated to above a melting point of the adhesive material. The adhesive material is cooled to below a melting point of the adhesive material to provide an adhesive bond that retains the stent to the catheter during vascular delivery, wherein the stent is released from the balloon following inflation and deflation of the balloon at a treatment site.

Another aspect of the present invention is a system for treating a vascular condition, comprising a catheter and a stent. The catheter includes an inflatable balloon. The stent is removably coupled to the balloon with an adhesive material that has been heated to above a melting point of the adhesive material and cooled to below a melting point of the adhesive material to provide an adhesive bond that retains the stent to the catheter during vascular delivery, wherein the stent is released from the balloon following inflation and deflation of the balloon at a treatment site.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 2 is a flow diagram of one embodiment of a method of manufacturing a system for treating a vascular condition, in accordance with the present invention;

FIG. 3 is a flow diagram of another embodiment of a method of manufacturing a system for treating a vascular condition, in accordance with the present invention; and FIG. 4 is a flow diagram of yet another embodiment of a method of manufacturing a system for treating a vascular condition, in accordance with the present invention.

DETAILED DESCRIPTION OF THE PRESENTLY PREFERRED EMBODIMENTS

Figure 1:
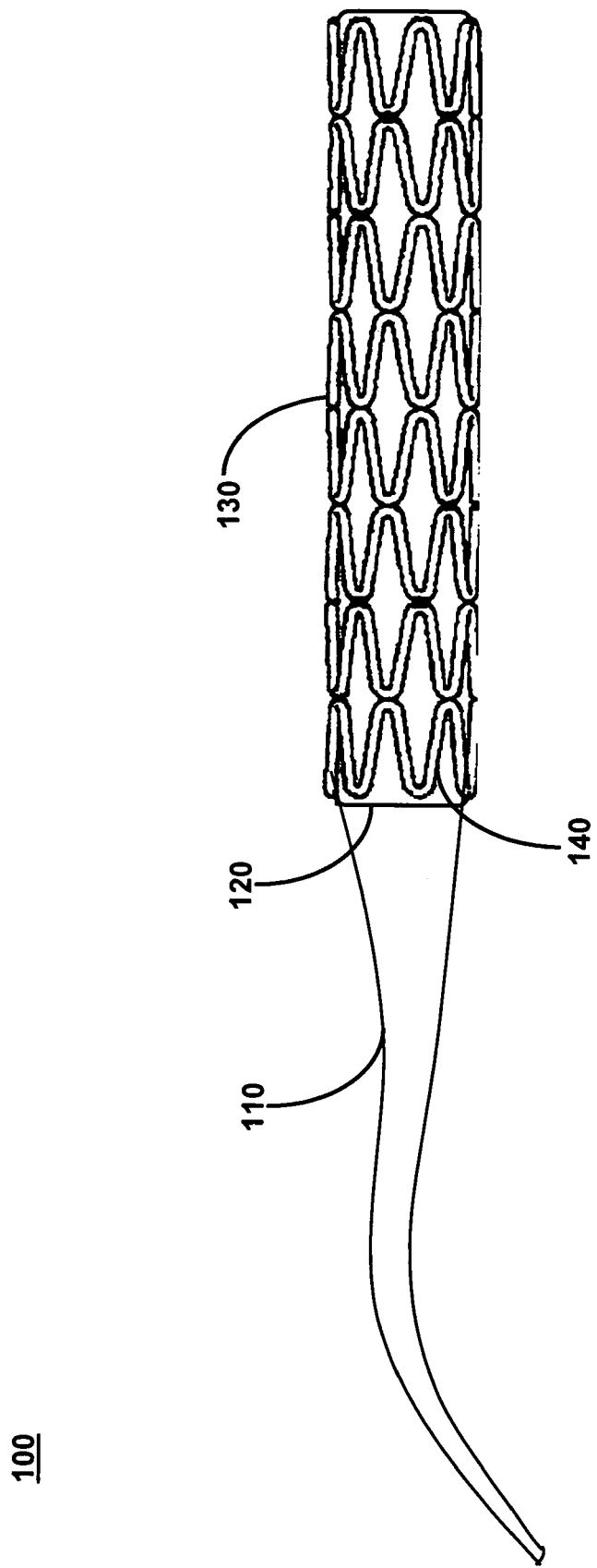
FIG. 1 is an illustration of one embodiment of a system for treating a vascular condition, in accordance with the present invention.

One aspect of the present invention is a system for treating a vascular condition. One embodiment of the system, in accordance with the present invention, is illustrated in FIG. 1 at 100. System 100 comprises a catheter 110, which includes an inflatable balloon 120, and a stent 130 that is releasably coupled to balloon 120 with an adhesive material 140.

Catheter 110 may be any catheter known in the art that is appropriate for delivering a stent to a lesion site, for example a percutaneous transluminal coronary angioplasty (PTCA) balloon catheter. Inflatable balloon 120, which expands the stent once it has been delivered, may be made of a suitable material such as polyethylene, polyethylene terephthalate (PET), or from nylon or the like. The length and diameter of balloon 120 may be selected based on the dimensions of the stent being delivered.

Stent 130 is releasably coupled to balloon 120, and thereby to catheter 110, with an adhesive material 140. Stent 130 may be made of a wide variety of medical implantable materials, including, but not limited to, stainless steel, nitinol, tantalum, ceramic, nickel, titanium, aluminum, polymeric materials, MP35N, stainless steel, titanium ASTM F63-83 Grade 1, niobium, high carat gold K 19–22, and combinations of the above. The stent may be formed with openings in its walls, such as spaces between portions of the wire in the case of a wire coil stent or holes in the case of a tubular stent.

Adhesive material 140 is a biocompatible material having a melting point below that of the balloon material, for example below approximately one hundred sixty-five degrees Fahrenheit (165° F.). One such material is poly(ethylene oxide), which has a melting point between one hundred forty degrees Fahrenheit (140° F.) and one hundred sixty degrees Fahrenheit (160° F.).

To create the present system, adhesive material 140 has been heated to above its melting point and then cooled such that it forms weak adhesion points at the stent-balloon interface and, thus, a weak bond between stent 130 and balloon 120. The adhesive may, for example, have been heated at a temperature of approximately one hundred sixty-five degrees Fahrenheit (165° F.) for a time duration of approximately three minutes and then cooled to room temperature. The bond is strong enough to retain the stent to the balloon during vascular delivery, while still being weak enough to allow the stent to be released following inflation and deflation of the balloon at a treatment site.

Another aspect of the present invention is a method of manufacturing a system for treating a vascular condition. FIG. 2 shows a flow diagram of one embodiment in accordance with the present invention at 200.

In this embodiment, a catheter is provided, the catheter including an inflatable balloon (Block 205). The catheter may be any catheter known in the art that is appropriate for delivering a stent to a lesion site identified for treatment, for example a percutaneous transluminal coronary angioplasty (PTCA) balloon catheter. The balloon may be made from a suitable material such as polyethylene, polyethylene terephthalate (PET), or from nylon or the like. The length and diameter of the balloon may be selected based on the dimensions of the stent being delivered.

The balloon is folded or otherwise manipulated or treated to minimize its profile (Block 210). A stent is positioned over the balloon by, for example, slipping the stent over the folded balloon (Block 215). A sheath made of a material such as polytetrafluoroethylene (PTFE) or the like is then positioned over the stent (Block 220), thereby enclosing both the stent and the balloon.

An adhesive material is dispersed throughout a fluid (Block 225). The adhesive material may comprise a biocompatible material having a melting point below that of the balloon material, for example below approximately one hundred sixty-five degrees Fahrenheit (165° F.). One such material is poly(ethylene oxide), which has a melting point between one hundred forty degrees Fahrenheit (140° F.) and one hundred sixty degrees Fahrenheit (160° F.). The poly(ethylene oxide) may be dispersed in a fluid such as water to form a dilute solution. For example, one gram (1 g) of poly(ethylene oxide) may be dispersed in one hundred cubic centimeters (100 cc) of water.

The adhesive material is applied between the inner surface of the stent and the outer surface of the balloon by introducing the adhesive material within the sheath (Block 230). This may be accomplished by, for example, injecting a dilute solution of poly(ethylene oxide) within a PTFE sheath such that it flows between the inner surface of the stent and the outer surface of the balloon. Where the stent is formed with openings in its walls, the sheath may aid both in directing the adhesive material between the stent and the balloon and in containing the material so it remains in place during the following steps.

The stent is then crimped onto the balloon (Block 235). The sheath may additionally provide protection for the stent during the crimping process, reducing the risk of damage to the stent.

The balloon is pressurized with an inflation pressure of, for example, approximately seventy pounds per square inch (70 PSI), thereby maintaining the balloon in a partially inflated configuration during the following heating and cooling steps (Block 240). Partially inflating the balloon provides good contact between the balloon and the stent and may cause the balloon to protrude through openings formed in the wall of the stent or at either end of the stent, improving stent retention. The interior diameter of the sheath may aid in defining the shape and size of any balloon protrusions, which may be permanently set by the following heating and cooling steps.

The adhesive material is heated to above its melting point (Block 245). This may be accomplished by, for example, heating the assembly described above in a heat set block at a temperature of approximately one hundred sixty-five degrees Fahrenheit (165° F.) for approximately three minutes.

The adhesive material is then cooled to below its melting point, for example by removing the assembly from the heat set block and allowing it to cool at room temperature (Block 250). Once the assembly has cooled, the inflation pressure is discontinued (Block 255), and the sheath is removed from the assembly (Block 260). Alternatively, the sheath may be left on the assembly for protection during shipping or storage.

Upon cooling, the adhesive material forms weak adhesion points at the stent-balloon interface and, thus, a weak bond between the stent and the balloon. This bond retains the stent to the balloon during vascular delivery, while still allowing the stent to be released following inflation and deflation of the balloon at a treatment site. Maintaining the balloon in a partially expanded configuration during the heating and cooling steps may contribute to the adhesive bond formed between the stent and balloon.

FIG. 3 shows a flow diagram of another embodiment of a method of manufacturing a system for treating a vascular condition, in accordance with the present invention at 300.

In this embodiment, a catheter is provided, the catheter including an inflatable balloon (Block 305). The catheter may be any catheter known in the art that is appropriate for delivering a stent to a lesion site identified for treatment, for example a percutaneous transluminal coronary angioplasty (PTCA) balloon catheter. The balloon may be made from a suitable material such as polyethylene, polyethylene terephthalate (PET), or from nylon or the like. The length and diameter of the balloon may be selected based on the dimensions of the stent being delivered.

A stent is positioned over the balloon by, for example, slipping the stent over the balloon (Block 310). An adhesive material is applied between an inner surface of the stent and an outer surface of the balloon (Block 315). The adhesive material may comprise a biocompatible material having a melting point below that of the balloon material, for example below approximately one hundred sixty-five degrees Fahrenheit (165° F.). One such material is poly(ethylene oxide), which has a melting point between one hundred forty degrees Fahrenheit (140° F.) and one hundred sixty degrees Fahrenheit (160° F.). The adhesive material may be applied by methods including, but not limited to, injecting, spraying, blowing, dipping, and the like.

The adhesive material is heated to above its melting point (Block 320). This may be accomplished by, for example, heating the system to a temperature of approximately one hundred sixty-five degrees Fahrenheit (165° F.) in a heat set block. The system is then cooled to below the melting point of the adhesive material by, for example, allowing it to cool at room temperature (Block 325).

Upon cooling, the adhesive material forms weak adhesion points at the stent-balloon interface and, thus, a weak bond between the stent and the balloon. This bond retains the stent to the balloon during vascular delivery, while still allowing the stent to be released following inflation and deflation of the balloon at a treatment site.

FIG. 4 is a flow diagram of yet another embodiment of a method of manufacturing a system for treating a vascular condition, in accordance with the present invention at 400.

In this embodiment, a catheter is provided, the catheter including an inflatable balloon (Block 405). The catheter may be any catheter known in the art that is appropriate for delivering a stent to a lesion site identified for treatment, for example a percutaneous transluminal coronary angioplasty (PTCA) balloon catheter. The balloon may be made from a suitable material such as polyethylene, polyethylene terephthalate (PET), or from nylon or the like. The length and diameter of the balloon may be selected based on the dimensions of the stent being delivered.

The balloon is folded or otherwise manipulated or treated to minimize its profile (Block 410). For example, the balloon may be tightly wrapped about the catheter. A stent is positioned over the balloon (Block 415). The stent may be crimped onto the balloon to ensure the stent fits snugly against the balloon (Block 420). A sheath made of a material such as polytetrafluoroethylene (PTFE) or the like is then positioned over the stent (Block 425), thereby enclosing both the stent and the balloon and retaining the stent in a tight interference fit on the wrapped balloon. The sheath may comprise a single tubular member or it may comprise a plurality of tubular members.

An adhesive material is dispersed throughout a fluid (Block 430). The adhesive material may comprise a biocompatible material having a melting point below that of the balloon material, for example below approximately one hundred sixty-five degrees Fahrenheit (165° F.). One such material is poly(ethylene oxide), which has a melting point between one hundred forty degrees Fahrenheit (140° F.) and one hundred sixty degrees Fahrenheit (160° F.). The poly(ethylene oxide) may be dispersed throughout a fluid such as water to form a solution. For example, three grams (3 g) of poly(ethylene oxide) may be dispersed in twenty cubic centimeters (20 cc) of water. To dissolve the adhesive material in the water, the adhesive material and fluid are heated, for example to a temperature in the range of ninety-five degrees Fahrenheit (95° F.) to one hundred five degrees Fahrenheit (105° F.) for a time duration of approximately ninety (90) minutes (Block 435).

The adhesive material is applied between the inner surface of the stent and the outer surface of the balloon. This may be accomplished by, for example, loading the adhesive solution, comprising the adhesive material dissolved in the water, into a syringe having a fine needle (Block 440), inserting the needle within the sheath (Block 445), and injecting the adhesive solution at high pressure through the needle within the sheath such that the adhesive material coats at least a portion of the outer surface of the balloon (Block 450). Where the stent is formed with openings in its walls, the sheath may aid both in directing the adhesive material between the stent and the balloon and in containing the material so it remains in place during the following steps.

The stent is then again crimped onto the balloon (Block 455), and the balloon is pressurized with an inflation pressure of, for example, approximately seventy pounds per square inch (70 PSI), thereby maintaining the balloon in a partially inflated configuration during the following heating and cooling steps (Block 460). Partially inflating the balloon provides good contact between the balloon and the stent and may cause the balloon to protrude through openings formed in the wall of the stent or at either end of the stent, improving stent retention. The interior diameter of the sheath may aid in defining the shape and size of any balloon protrusions, which may be permanently set by the following heating and cooling steps.

The adhesive material is heated to above its melting point (Block 465). This may be accomplished by, for example, heating the assembly described above in a heat set block at a temperature of approximately one hundred sixty-five degrees Fahrenheit (165° F.) for approximately three minutes.

The adhesive material is then cooled to below its melting point, for example by removing the assembly from the heat set block and allowing it to cool at room temperature (Block 470). Once the assembly has cooled, the inflation pressure is discontinued (Block 475), and the sheath is removed from the assembly (Block 480). Alternatively, the sheath may be left on the assembly for protection during shipping or storage.

Upon cooling, the adhesive material forms weak adhesion points at the stent-balloon interface and, thus, a weak bond between the stent and the balloon. This bond retains the stent to the balloon during vascular delivery, while still allowing the stent to be released following inflation and deflation of the balloon at a treatment site. Maintaining the balloon in a partially expanded configuration during the heating and cooling steps may contribute to the adhesive bond formed between the stent and balloon.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of manufacturing a system for treating a vascular condition, comprising:
    providing a catheter, the catheter including an inflatable balloon;
    positioning a stent over the balloon;
    positioning a sheath over the stent;
    crimping the stent onto the balloon prior to introducing an adhesive material within the sheath;
    dispersing an adhesive material throughout a fluid prior to application of the adhesive material wherein approximately three grams (3 g) of adhesive material is dispersed throughout approximately twenty cubic centimeters (20 cc) of fluid;
    applying an adhesive material between an inner surface of the stent and an outer surface of the balloon;
    heating the adhesive material to above a melting point of the adhesive material;

cooling the adhesive material to below a melting point of the adhesive material to provide an adhesive bond that retains the stent to the catheter during vascular delivery, wherein the stent is released from the balloon following inflation and deflation of the balloon at a treatment site; and removing the sheath after cooling the adhesive material.

2. A method of manufacturing a system for treating a vascular condition, comprising:
    providing a catheter, the catheter including an inflatable balloon;
    positioning a stent over the balloon;
    positioning a sheath over the stent;
    crimping the stent onto the balloon prior to introducing an adhesive material within the sheath;
    dispersing an adhesive material throughout a fluid prior to application of the adhesive material;
    heating the adhesive material and fluid to dissolve the adhesive material in the fluid;
    applying an adhesive material between an inner surface of the stent and an outer surface of the balloon;
    heating the adhesive material to above a melting point of the adhesive material;
    cooling the adhesive material to below a melting point of the adhesive material to provide an adhesive bond that retains the stent to the catheter during vascular delivery, wherein the stent is released from the balloon following inflation and deflation of the balloon at a treatment site; and
    removing the sheath after cooling the adhesive material.

3. The method of claim 2 wherein heating the adhesive material and fluid to dissolve the adhesive material in the fluid comprises heating the adhesive material to a temperature in the range of ninety-five degrees Fahrenheit (95° F.) to one hundred five degrees Fahrenheit (105° F.) for a time duration of approximately ninety (90) minutes.

4. A method of manufacturing a system for treating a vascular condition, comprising:
    providing a catheter, the catheter including an inflatable balloon;
    positioning a stent over the balloon;
    positioning a sheath over the stent;
    crimping the stent onto the balloon prior to introducing an adhesive material within the sheath;
    dispersing the adhesive material throughout a fluid prior to introduction of the adhesive material;
    introducing the adhesive material between an inner surface of the stent and an outer surface of the balloon wherein introducing the adhesive material comprises:
    loading the adhesive material into a syringe having a fine needle;
    inserting the needle within the sheath; and
    injecting the adhesive material through the needle within the sheath such that the adhesive material coats at least a portion of the outer surface of the balloon;
    heating the adhesive material to above a melting point of the adhesive material;
    cooling the adhesive material to below a melting point of the adhesive material to provide an adhesive bond that retains the stent to the catheter during vascular delivery, wherein the stent is released from the balloon following inflation and deflation of the balloon at a treatment site; and
    removing the sheath after cooling the adhesive material.

* * * * *